US012571752B2

(12) United States Patent
Okamoto et al.

(10) Patent No.: US 12,571,752 B2
(45) Date of Patent: Mar. 10, 2026

(54) OXYGEN SENSOR ELEMENT AND METHOD FOR MANUFACTURING SAME

(71) Applicants: NAGAOKA UNIVERSITY OF TECHNOLOGY, Nagaoka (JP); KOA CORPORATION, Ina (JP)

(72) Inventors: Tomoichiro Okamoto, Nagaoka (JP); Kenichi Iguchi, Ina (JP); Yukiko Ota, Ina (JP); Ryosuke Komatsu, Ina (JP); Tetsuro Tanaka, Ina (JP); Katsuhide Nishizawa, Ina (JP)

(73) Assignees: NAGAOKA UNIVERSITY OF TECHNOLOGY, Nagaoka (JP); KOA CORPORATION, Ina (JP)

( * ) Notice: Subject to any disclaimer, the term of this patent is extended or adjusted under 35 U.S.C. 154(b) by 352 days.

(21) Appl. No.: 18/567,069

(22) PCT Filed: Jun. 9, 2022

(86) PCT No.: PCT/JP2022/023308
§ 371 (c)(1),
(2) Date: Dec. 5, 2023

(87) PCT Pub. No.: WO2022/264918
PCT Pub. Date: Dec. 22, 2022

(65) Prior Publication Data
US 2024/0272107 A1    Aug. 15, 2024

(30) Foreign Application Priority Data
Jun. 17, 2021    (JP) ................................. 2021-101193

(51) Int. Cl.
*G01N 27/12*    (2006.01)
*G01N 33/00*    (2006.01)

(52) U.S. Cl.
CPC ....... *G01N 27/125* (2013.01); *G01N 33/0036* (2013.01)

(58) Field of Classification Search
CPC .......................... G01N 27/125; G01N 33/0036
(Continued)

(56) References Cited

U.S. PATENT DOCUMENTS 4,786,476 A * 11/1988 Munakata .............. G01N 27/12
           422/98
2003/0159928 A1* 8/2003 Kojima .............. G01N 27/4067
           204/408
(Continued)

FOREIGN PATENT DOCUMENTS

JP      H10-73549 A     3/1998
JP      2007-085816 A     4/2007
(Continued)

*Primary Examiner* — Peter J Macchiarolo
*Assistant Examiner* — Rodney T Frank
(74) *Attorney, Agent, or Firm* — Carrier, Shende & Associates P.C.; Fulchand P. Shende; Joseph P. Carrier

(57) ABSTRACT

An oxygen sensor element that can achieve electric power saving without losing sensor characteristics has a structure in which an outer surface of a ceramic sintered body as a sensing layer made of a composition $LnBa_2Cu_3O_{7-\delta}$ (Ln denotes rare earth element) is covered with heat insulating layers. A heat insulating material having a composition $Ln_2BaCuO_5$ is used for the heat insulating layers, and that composition $Ln_2BaCuO_5$ is added with 20 mol % of $LnBa_2Cu_3O_{7-\delta}$. This allows a sintering behavior of the heat insulating layers to come close to a sintering behavior of the sensing layer, and can thus prevent the occurrence of separation of the layers and cracks. The oxygen sensor element has a sandwich structure where the sensing layer is sandwiched between the heat insulating layers, thereby reducing
(Continued)

the amount of heat dissipated from the sensing layer, and making it possible to achieve electric power saving.

18 Claims, 7 Drawing Sheets

(58) Field of Classification Search
USPC ........................................................ 73/31.05
See application file for complete search history.

(56) References Cited

U.S. PATENT DOCUMENTS

| | | | | |
|---|---|---|---|---|
| 2004/0104114 A1* | 6/2004 | Schulte | .............. | G01N 27/4074 |
| | | | | 204/426 |
| 2015/0060274 A1* | 3/2015 | Ishikawa | ............ | G01N 27/4077 |
| | | | | 204/424 |
| 2021/0018456 A1 | 1/2021 | Ito et al. | | |
| 2022/0018804 A1* | 1/2022 | Tanaka | ................... | G01N 27/14 |
| 2023/0349851 A1 | 11/2023 | Tanaka et al. | | |
| 2024/0272107 A1* | 8/2024 | Okamoto | ............ | C04B 35/4504 |

FOREIGN PATENT DOCUMENTS

| | | |
|---|---|---|
| JP | 2019-168366 A | 10/2019 |
| JP | 2019-168367 A | 10/2019 |

\* cited by examiner

W. Wong-Ng, L.P. Cook, B. Paretzkin, M.D. Hill, J.K. Stalick,
J. Am. Ceram. Soc., 77 (1994) 2354-2362.

OXYGEN SENSOR ELEMENT AND METHOD FOR MANUFACTURING SAME

TECHNICAL FIELD

The present invention relates to an oxygen sensor element using a ceramic sintered body, and also relates to a method for manufacturing the oxygen sensor element.

BACKGROUND ART

An oxygen sensor using a ceramic sintered body has been conventionally utilized in order to detect oxygen concentration in the ambient atmosphere to be measured, for example, in gas. Such an oxygen sensor as described above uses composite ceramics generated by mixing $LnBa_2Cu_3O_{7-\delta}$ and $Ln_2BaCuO_5$ (Ln denotes rare earth element), for example, which are material compositions for the oxygen sensor, and also utilizes a hot spot phenomenon that a part of a wire material configuring the sensor is red-heated by applying a voltage.

From the viewpoints of usage environment, sensing performance, etc., it is desired that the oxygen sensor is small, light, and has a low cost and reduced power consumption. For example, Patent Document 1 discloses an oxygen sensor, wherein a hot spot portion of a sensor element is coated with a porous heat insulating material having low heat conductivity to decrease heat dissipation from the hot spot portion so as to reduce power consumption.

PRIOR ART DOCUMENTS

Patent Documents

Patent Document 1: JP H10-73549A

DISCLOSURE OF THE INVENTION

Problem to be Solved by the Invention

A configuration that the temperature of a heat generating portion is maintained is effective for an oxygen sensor to maintain its oxygen detecting function (sensing function). In Patent Document 1, a wire material configuring the oxygen sensor is partially constricted and thinned at a specific position where a hot spot is generated, and the constricted portion is covered with a heat insulating material. As the heat insulating material, alumina ($Al_2O_3$), magnesia (MgO), yttria ($Y_2O_3$), and barium titanate ($BaTiO_3$) are exemplified.

Forming a constricted portion at a specific position of the wire material of the oxygen sensor is effective to some extent for electric power saving by using a thin wire.

However, the wire material is more likely to be fused by a hot spot generated when driving the sensor. This results in a decrease in the mechanical strength, so that an oxygen sensor with high durability and reliability cannot be provided.

The heat insulating materials listed in Patent Document 1 are more likely to react with $LnBa_2Cu_3O_{7-\delta}$ (Ln denotes rare earth element, and δ denotes oxygen non-stoichiometry) that is a material for the sensor element during baking. This degrades the sensor sensitivity, and in addition, makes it difficult to bake the heat insulating material and the sensor element material simultaneously, which causes a problem that the mass productivity degrades. Furthermore, these heat insulating materials show different sintering behaviors from $LnBa_2Cu_3O_{7-\delta}$, and are thus more likely to separate from the sensor element material on the interface. This also causes a problem in terms of securing the sensor sensitivity of the oxygen sensor and a problem with the mass productivity.

In light of these problems, the present invention aims to provide an oxygen sensor element that can achieve electric power saving when driving an oxygen sensor without losing sensor characteristics of the oxygen sensor.

Means of Solving the Problem

The present invention aims to resolve the above problems, and includes the following structure, for example, as a means for achieving the above aim. That is, the present invention is an oxygen sensor element characterized in that it is made of a ceramic sintered body for detecting oxygen concentration based on an electric current value or a resistance value measured when a voltage is applied to electrodes provided at either end portion of the ceramic sintered body. Heat insulating layers represented as a composition formula $Ln_2BaCuO_5$ (Ln denotes rare earth element) are arranged so as to cover a predetermined portion on an outer surface of the ceramic sintered body, excluding the electrodes.

For example, it is characterized that the heat insulating layers are added with a co-material represented as a composition formula $LnBa_2Cu_3O_{7-\delta}$ (Ln denotes rare earth element, and δ denotes oxygen non-stoichiometry). For example, it is characterized in that an addition quantity "a" [mol %] of the co-material is $0 < a \leq 25$. It is also characterized in that the Ln is Nd (neodymium). It is further characterized in that, for example, the oxygen sensor element has a layered structure in which an outer surface of the ceramic sintered body excluding the electrodes is sandwiched between the heat insulating layers bidirectionally, and a part of the ceramic sintered body is exposed. It is also characterized in that a thickness t1 [μm] of the ceramic sintered body in a layered direction is $10 \leq t1 \leq 200$, and thicknesses t2 and t3 [μm] of the respective heat insulating layers, between which the ceramic sintered body is sandwiched, in the layered direction are $50 \leq (t2, t3) \leq 400$. For example, it is characterized in that the oxygen sensor element has a structure in which an outer surface of the ceramic sintered body excluding the electrodes is covered in its entirety with the heat insulating layer. It is further characterized in that, for example, the ceramic sintered body is formed into a linear shape.

Further, the oxygen sensor according to the present invention is characterized in that the oxygen sensor element described above functions as an oxygen concentration detecting element. For example, it is characterized in that the oxygen sensor element is stored in a protecting tube having air holes on either end.

Further, the present invention is a method for manufacturing an oxygen sensor element having a structure in which a predetermined portion on an outer surface of a ceramic sintered body as a sensing layer is covered with heat insulating layers, characterized in that the method includes the steps of: molding slurries, which are formed respectively by mixing raw materials for the ceramic sintered body together and by mixing raw materials for the heat insulating layers together, into a sheet form to manufacture a first sheet member and second sheet members; cutting each of the first sheet member and second sheet members into a predetermined size; layering the cut first sheet member and second sheet members so as to have respective predetermined thicknesses to form a layered body with the layered first sheet member sandwiched between the layered second sheet members in a vertical direction; cutting the layered body into a predetermined size and a predetermined shape to manufacture a sensor element; baking the sensor element; and forming a pair of electrodes on either end portion of the baked sensor element. In the baking step, the first sheet member and second sheet members are baked simultaneously.

Results of the Invention

According to the present invention, a sintering behavior of a sensor material for a sensing layer and a sintering behavior of a heat insulating material for heat insulating layers are close to each other, which makes it possible for an oxygen sensor element having a layered structure in which the sensing layer is sandwiched between the heat insulating layers to bake the heat insulating material and the sensor element material simultaneously, and to ensure the mass productivity. It is also possible to achieve electric power saving by improving heat insulating properties for the sensing layer.

DESCRIPTION OF EMBODIMENTS

An embodiment according to the present invention is described in detail below with reference to accompanying drawings. The oxygen sensor element according to the embodiment is comprised of a ceramic sintered body, where the sintered body is connected to a power source, thereby electric current flowing through the sintered body, and resulting in the central portion of the sintered body generating high-temperature heat. Heat-generating place (called hot spot) thereof functions as an oxygen concentration detector. The oxygen sensor element detects oxygen concentration based on the electric current value of current flowing through the ceramic sintered body or oxygen sensor element.

Figure 1:
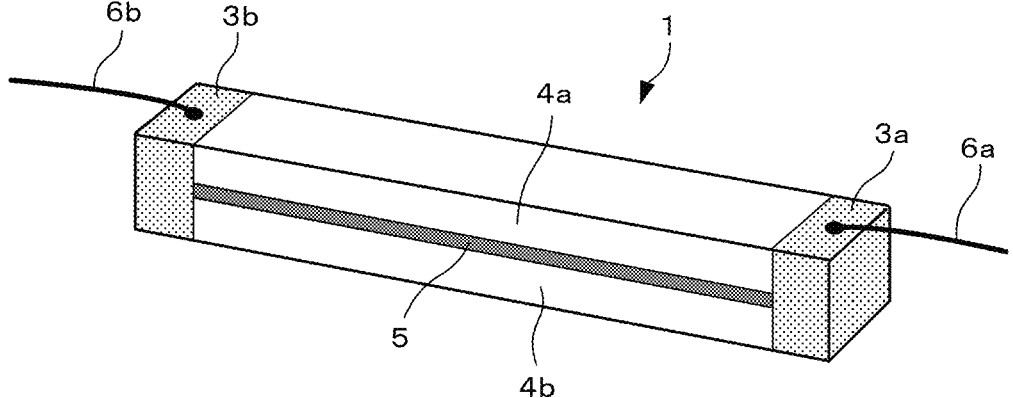
FIG. 1 is an external perspective view of an oxygen sensor element according to an embodiment of the present invention.

FIG. 1 is an external perspective view of the oxygen sensor element according to the embodiment. An oxygen sensor element 1 shown in FIG. 1 includes a sensing layer 5 having an oxygen detecting function (oxygen sensing function), two heat insulating layers 4a and 4b between which the sensing layer 5 is sandwiched bidirectionally (in the vertical direction), a pair of electrode portions 3a and 3b formed at longitudinally opposite end portions of a layered body (sensor element) formed by layering the sensing layer 5 and the heat insulating layers 4a and 4b, and lead wires 6a and 6b attached to the electrode portions 3a and 3b, respectively.

The sensing layer 5 is made from a composition $NdBa_2Cu_3O_{7-\delta}$ as a sensor material, which is generated by assigning Nd (neodymium), for example, as Ln in the composition $LnBa_2Cu_3O_{7-\delta}$ (Ln denotes rare earth element, and $\delta$ denotes oxygen non-stoichiometry).

The heat insulating layers 4a and 4b have heat insulating properties and are electrically insulating layers. For example, the heat insulating layers 4a and 4b are made from a composition generated by adding 20 mol % of $NdBa_2Cu_3O_{7-\delta}$ as a co-material to the composition $Nd_2BaCuO_5$ generated by assigning Nd (neodymium) as Ln in the composition $Ln_2BaCuO_5$.

Note that hereinafter, the composition $NdBa_2Cu_3O_{7-\delta}$ is described as "Nd123," the composition $Nd_2BaCuO_5$ is described as "Nd211," and the composition generated by adding 20 mol % of $NdBa_2Cu_3O_{7-\delta}$ to the composition $Nd_2BaCuO_5$ is described as "Nd211-20 mol % Nd123" as appropriate.

Here, while Nd (neodymium) is exemplified as Ln (rare earth element) of the oxygen sensor element material, any other rare earth element can be used. That is, as rare earth element, e.g., Sc (scandium), Y (yttrium), La (lanthanum), Sm (samarium), Eu (europium), Gd (gadolinium), Dy (dysprosium), Ho (holmium), Er (erbium), Tm (thulium), Yb (ytterbium), Lu (lutetium), etc., can be used.

Figure 2:
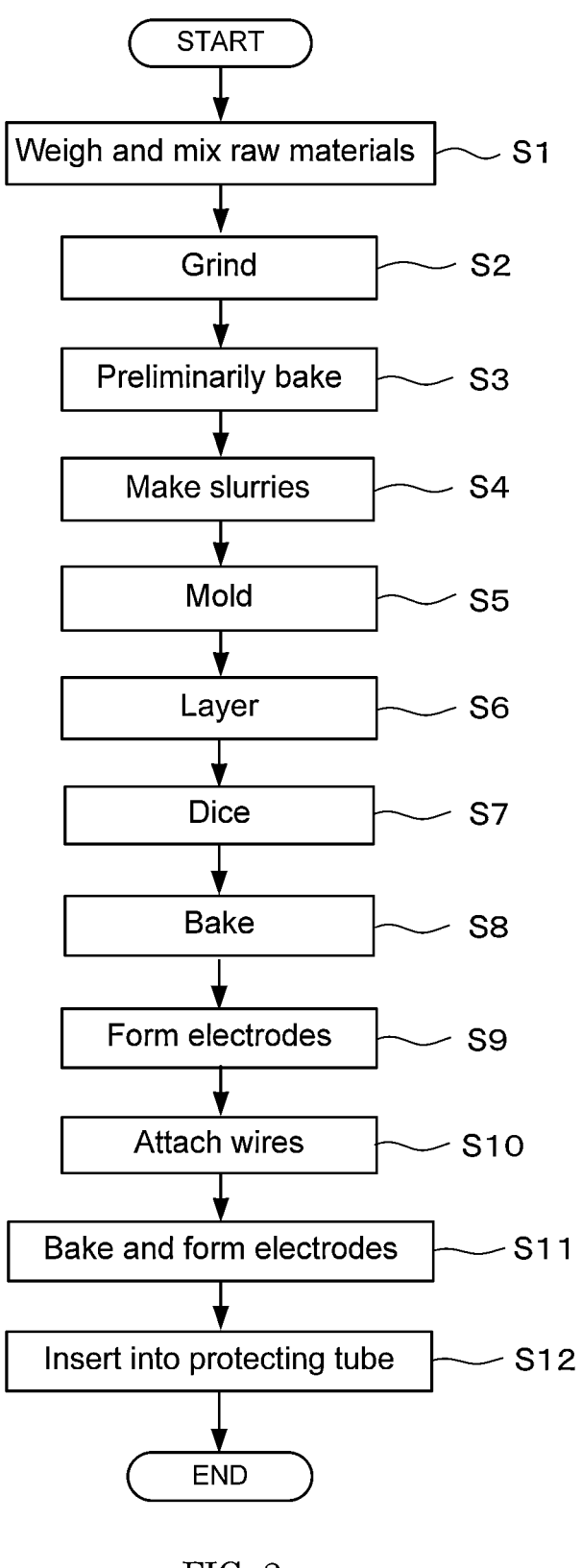
FIG. 2 is a flowchart illustrating in a time series the manufacturing process of the oxygen sensor element according to the embodiment and an oxygen sensor using the oxygen sensor element.

Next, an oxygen sensor element according to the embodiment and a method for manufacturing an oxygen sensor using the oxygen sensor element are described. FIG. 2 is a flowchart illustrating in a time series the manufacturing process of the oxygen sensor element according to the embodiment and the oxygen sensor using the oxygen sensor element.

In Step S1 of FIG. 2, Nd203, $BaCO_3$, and CuO, for example, are weighed using an electronic analytical scale and mixed together as raw materials for the oxygen sensor element so as to make the composition $NdBa_2Cu_3O_{7-\delta}$ (Nd123: raw material 1) and the composition $Nd_2BaCuO_5$ (Nd211: raw material 2).

In Step S2, the raw materials 1 and 2 for the oxygen sensor element weighed and mixed together in Step S1 described above are ground using a ball mill. Grinding may also be carried out using a solid phase method or a liquid phase method, such as with a bead mill using beads as grinding media.

In subsequent Step S3, the ground material (powder of the raw materials 1 and 2) described above is heat processed (preliminary baking) at 900° C. for 5 hours in atmospheric air. Preliminary baking is a process for adjusting reactivity and grain size. Temperature for the preliminary baking may be 880 to 970° C., and is more preferably 900 to 935° C.

As described above, the raw materials 1 and 2 preliminarily baked in such a manner as described above are ground using a ball mill, etc., to have equal grain size, and thereafter a slurry is made in Step S4. The vehicle generated by mixing a binder resin (e.g., polyvinyl butyral (PVB)) and a solution (e.g., toluene) together is kneaded and mixed with the preliminarily baked raw materials so as to make a slurry.

More specifically, the preliminarily baked powder of the raw material 1 (Nd123) is mixed with the vehicle to make a first slurry, and the preliminarily baked powder (Nd211-20 mol % Nd123) of the raw material 2 (Nd211) added with 20 mol % of Nd123 is mixed with the vehicle to make a second slurry.

In subsequent Step S5, each of the first and second slurries is molded into a sheet form having a thickness of 30 μm by a doctor blade method, for example, to respectively manufacture a first sheet member that is used for the sensing layer described above, and a second sheet member that is used for the heat insulating layers described above.

Note that as a method for molding a slurry into a sheet form, the slurry is molded by applying with a pressing pressure using a uniaxial press method, hydrostatic pressing method, hot pressing method, printing method, or thin film method, for example, so as to manufacture a plate member (press-molded body) having a predetermined thickness. Particularly, a dipping method, printing method, and thin film method are applicable to the second sheet members that are used for the heat insulating layers.

Figure 3:
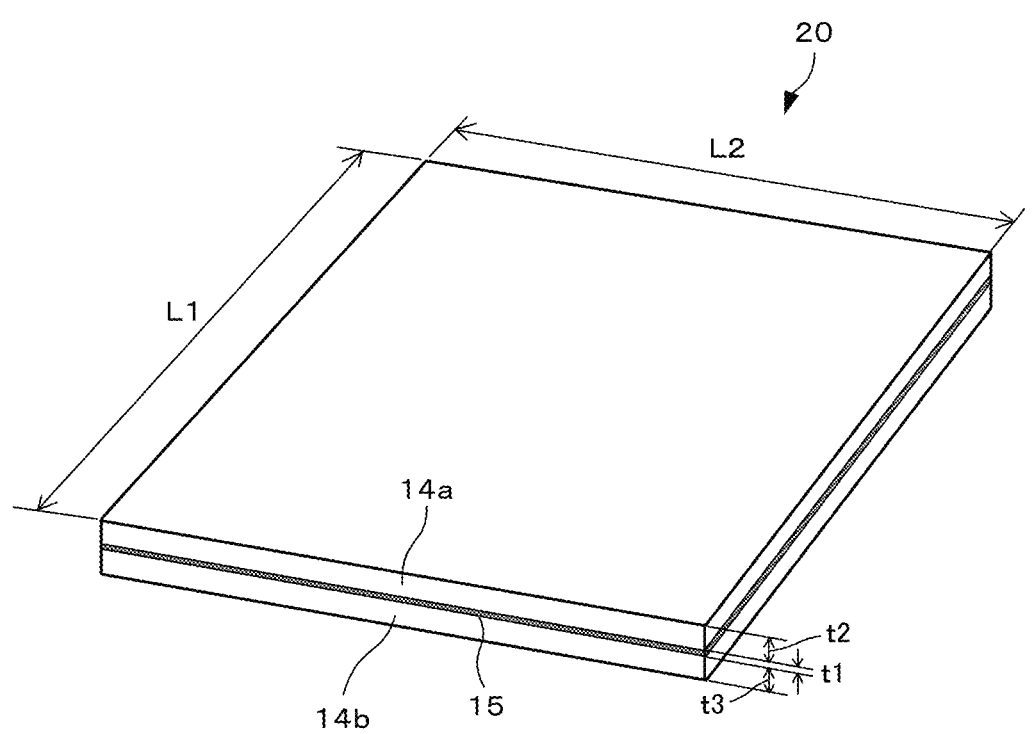
FIG. 3 is an external perspective view of a plate member manufactured by cutting a sheet member for a sensing layer and a sheet member for heat insulating layers and layering the sheets.

In Step S6, the first sheet member and the second sheet members manufactured in Step S5 described above are layered respectively to manufacture a layered sheet (layered body) 20 shown in FIG. 3. More specifically, after each of the first and second sheet members is cut into a size of L1 (100 mm)×L2 (100 mm) for example, the first sheet member is layered so as to have a thickness t1 of 30 μm, for example, to form a sensing layer as shown by reference numeral 15 in FIG. 3, and then for forming heat insulating layers 14a and 14b, the second sheet members which sandwich the first sheet member between them in the vertical direction are layered so as to have thicknesses t2 and t3 of 160 μm respectively, for example.

Note that when focus is on the characteristics of an oxygen sensor element, the thicknesses of the sensing layer and the heat insulating layers are not limited to those given above. For example, if the thickness t1 of the sensing layer is less than 10 μm, the resistance value becomes too high, which makes it difficult to secure the heat generation amount when a hot spot is generated. Moreover, the current density increases significantly, which degrades the durability. On the other hand, if the thickness t1 is greater than 200 μm, an increase in electric current value causes power consumption to excessively increase when driving the oxygen sensor. In view of this, it is preferable that the thickness t1 of the sensing layer is 10 to 200 μm, and more preferably the thickness t1 is 30 to 120 μm.

If the thicknesses t2 and t3 of the heat insulating layers are less than 50 μm, the heat insulating properties become less effective. If the thicknesses t2 and t3 of the heat insulating layers are greater than 400 μm, this affects the response speed of an oxygen sensor. Therefore, it is preferable that the thicknesses of the heat insulating layers are 50≤(t2, t3)≤400 μm, and more preferably the thicknesses are 100≤(t2, t3)≤250 μm.

Dicing is carried out in Step S7. More specifically, the layered sheet (layered body) shown in FIG. 3, which has been layered in Step S6 described above is cut into a shape of rod-like body having cross-sectional dimensions of 0.35 mm×0.35 mm and a length of 5 mm, for example, in accordance with the size and shape of the oxygen sensor described later.

In Step S8, de-binding of the oxygen sensor element that has been diced in such a manner as described above is performed, and the resulting oxygen sensor element is baked in atmospheric air at, for example, 980° C. for 10 hours. While the firing temperature may range from 900 to 1020° C., the firing temperature may be changed according to composition. An annealing step may be carried out after the baking.

In Step S9, both end portions of the resulting oxygen sensor element are dipped and coated in sliver (Ag), and dried at 150° C. for 10 minutes, thereby forming the electrodes 3a and 3b as shown in FIG. 1. In Step S10, a silver (Ag) wire having a diameter of 0.1 mm, for example, is attached through a joining method such as wire bonding to the electrodes formed in Step S9 and then dried at 150° C. for 10 minutes. The terminal electrodes formed in this manner are then baked at 670° C. for 20 minutes, for example, in Step S11 (electrode baking).

Material of the electrodes and the wire is not limited to silver (Ag) described above, and the electrodes and the wire may be of a material such as gold (Au), platinum (Pt), nickel (Ni), tin (Sn), copper (Cu), resin electrode, etc. Moreover, for forming the electrodes, a printing method or a film adhering method such as sputtering may also be used. Furthermore, electrical characteristics of the oxygen sensor element manufactured through the steps described above may also be evaluated using a four-terminal method, for example.

Figure 4:
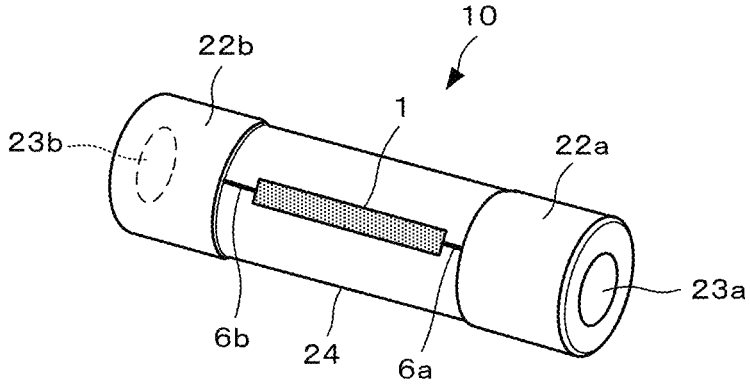
FIG. 4 is an external perspective view of the oxygen sensor using the oxygen sensor element according to the embodiment.

In Step S12, the oxygen sensor element manufactured in the steps described above is inserted into a protecting tube (cylindrical glass tube) 24 which is made of heat-resistant glass and functions as a protecting member for the oxygen sensor element 1, as shown in FIG. 4, for example. The end parts of the respective lead wires of the oxygen sensor element 1 that has been inserted in the tube are connected by lead-free solder, for example, to metal conductive caps (mouthpieces) 23a and 23b fit on either end of the protecting tube 24.

A specific configuration of the oxygen sensor having the oxygen sensor element stored in the protecting tube in such a manner as described above is explained later.

Next, evaluation results of sensor characteristics, etc., measured on a test sample of the oxygen sensor element according to the embodiment are described.

<Sintering Behavior Evaluation Results>

The oxygen sensor element according to the embodiment has a structure (sandwich structure) in which the sensing layer is sandwiched vertically between two heat insulating layers made of material different from the material for the sensing layer.

Therefore, when these layers are baked simultaneously, there is a concern that separation of the layers, etc. may occur due to differences in sintering behavior.

Figure 5:
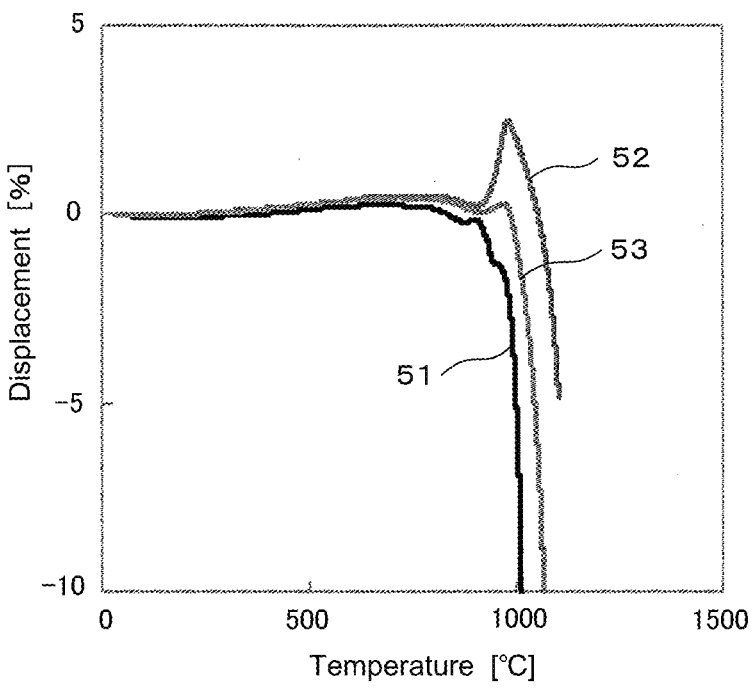
FIG. 5 is a diagram showing measurement results 1 of a sintering behavior of a test sample of the oxygen sensor element according to the embodiment.
Figure 6:
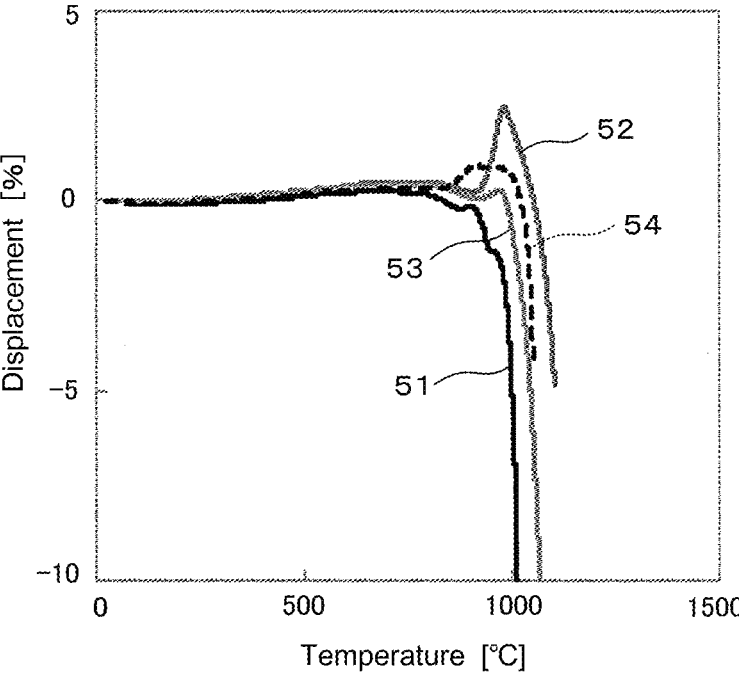
FIG. 6 is a diagram showing measurement results 2 of the sintering behavior of the test sample of the oxygen sensor element according to the embodiment.

Sintering behaviors of test samples of the oxygen sensor element according to the embodiment are measured using thermomechanical analysis (TMA). The measurement results are shown in FIGS. 5 and 6. Note that in FIGS. 5 and 6, the horizontal axis represents the temperature [C], while the vertical axis represents the displacement [%].

[Evaluation Result 1]

The characteristics shown by reference numeral 51 in FIG. 5 are the measurement results of the sintering behavior of Nd123 (composition NdBa$_2$Cu$_3$O$_{7-\delta}$). The characteristics shown by reference numeral 52 are the measurement results of the sintering behavior of Nd211 (composition Nd$_2$BaCuO$_5$). Reference numeral 53 shows the measurement results of the sintering behavior of Nd211-20 mol % Nd123 (composition generated by adding 20 mol % of NdBa$_2$Cu$_3$O$_{7-\delta}$ to the composition Nd$_2$BaCuO$_5$).

It is understood from the measurement results of the sintering behaviors using TMA that the sintering behavior of the material made by adding 20 mol % of Nd123 to Nd211 comes close to the sintering behavior of Nd123. This shows that although the sintering temperature of Nd211 is higher compared to Nd123, the addition of Nd123 to Nd211 caused the sintering temperature of Nd211 to shift to the lower temperature side.

Therefore, even if a sensing layer made of the material Nd123 and a heat insulating layer made of the material Nd211-20 mol % Nd123 are baked simultaneously, their sintering behaviors are the same and thus a stress is less likely to be generated on the interface. As a result, it is understood that the occurrence of separation of the layers and cracks can be prevented due to absence of strain, stress, etc., thereby improving the mass productivity of the oxygen sensor element.

The reasons why separation of the layers did not occur as described above may be thought that both the heat insulating layer and the sensing layer are made of porous material, and thus the sintering density is kept low. The fact that the heat insulating layer and the sensing layer are porous does not affect the sensing function of the oxygen sensor element.

[Evaluation Result 2]

Further, a sintering behavior of a composition having a different substitution quantity of Nd as a material for the sensing layer was measured. Sintering behavior of the composition Nd$_{1.4}$Ba$_{1.6}$Cu$_3$O$_{7-\delta}$ (this composition is appropriately described as Nd123_x-0.4) obtained by making a substitution quantity "x" of Nd in the composition Nd$_{1+x}$Ba$_{2-x}$Cu$_3$O$_{7-\delta}$ be 0.4, was measured using thermomechanical analysis (TMA). The measurement results are shown in FIG. 6.

As shown by a dotted line 54 in FIG. 6, the material of the composition Nd123_x-0.4 allowed its sintering behavior to come even closer to the sintering behavior of Nd211-20 mol % Nd123 (shown by reference numeral 53) while maintaining the resistivity described later. Nd123_x-0.4 has a composition generated by Nd substitution in Nd123 that is a material for the sensing layer, and shows that the firing temperature shifts to the higher temperature side by substituting Nd for Ba.

According to the above evaluation results 1 and 2, it is considered from the viewpoints of simultaneous baking, etc. for the oxygen sensor element, a combination of Nd123_x-0.4 as a material for the sensing layer, which also has moisture resistance, and Nd211-20 mol % Nd123 as a material for the heat insulating layers is optimal, which leads to further improvement in the mass productivity of the oxygen sensor element.

Figure 8:
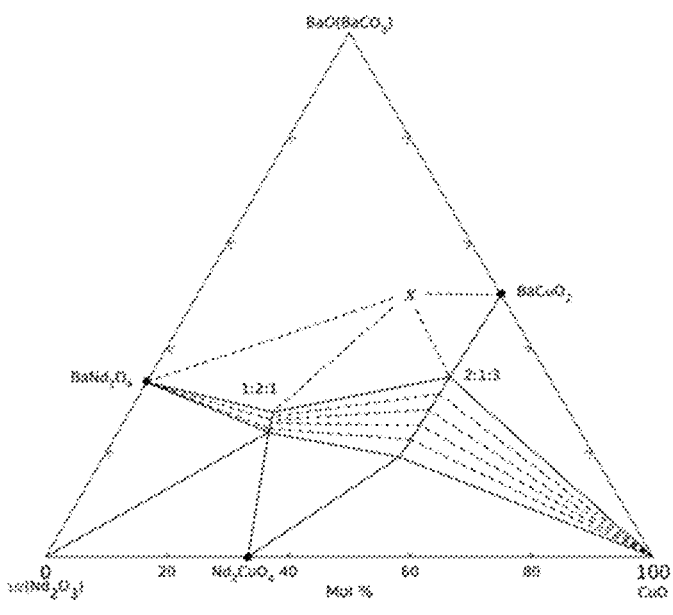
FIG. 8 is a phase diagram showing that Nd211 and Nd123 can coexist.

The material (Nd123_x-0.4) for the sensing layer and the material (Nd211-20 mol % Nd123) for the heat insulating layers have equal reactivity. It could be confirmed that even when the sensing layer and the heat insulating layers are layered in a sandwich structure, these layers still do not react with each other or separate from each other. Furthermore, referring to the phase diagram shown in FIG. 8, it is understood that Nd211 and Nd123 can coexist and do not react with each other during baking.

Note that in the above descriptions, as a material for the heat insulating layers, a material made by adding 20 mol % of LnBa$_2$Cu$_3$O$_{7-\delta}$ as a co-material to the composition Ln$_2$BaCuO$_5$ is exemplified, however, provided that the addition quantity "a" [mol %] of this co-material falls within the range of $0 < a \leq 25$, desired heat insulating and electrical insulating effects can be obtained. If the addition quantity "a" exceeds 25 mol %, percolation causes a conductive path of LnBa$_2$Cu$_3$O$_{7-\delta}$ to be formed inside the heat insulating layers, so the electrical insulating function is lost and power consumption increases.

<Evaluation Results of Temperature Dependence of Resistivity>

Figure 7:
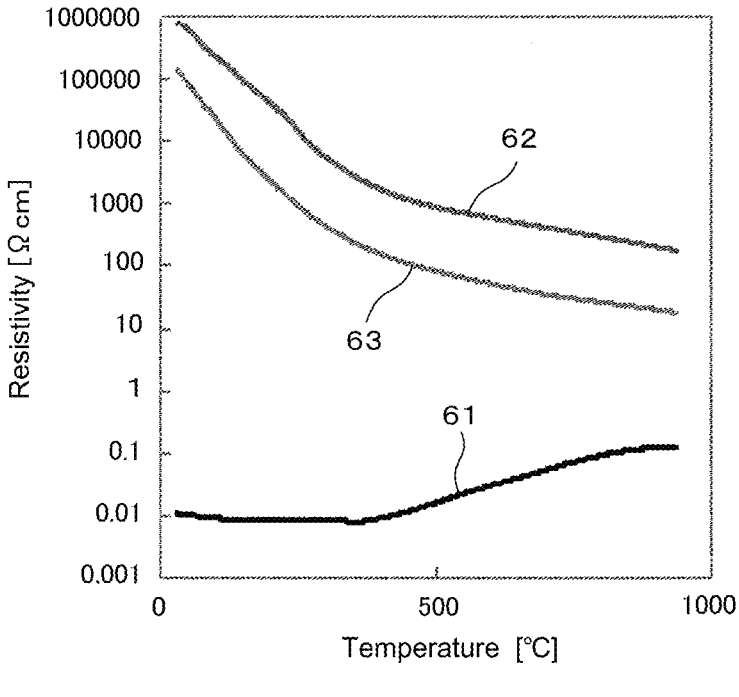
FIG. 7 is a diagram showing evaluation results of temperature dependence of a resistivity measured on the test sample of the oxygen sensor element according to the embodiment.

FIG. 7 shows the evaluation results of temperature dependence of a resistivity measured on the test sample of the oxygen sensor element according to the embodiment. In FIG. 7, the horizontal axis represents the temperature [° C.], while the vertical axis represents the resistivity [Ωcm].

As shown in FIG. 7, as for a material for the heat insulating layers, Nd211 shown by reference numeral 62 had a higher resistivity than the resistivity of Nd211-20% Nd123 shown by reference numeral 63. Both Nd211 and Nd211-20% Nd123 exhibit semiconductor-like characteristics that the resistivity decreases as the temperature increases.

On the other hand, it is understood that Nd123 shown by reference numeral 61 in FIG. 7, which is a material for the sensing layer, has a low resistivity and thus allows electric current to easily flow through the material. Focusing on the actual usage temperature of the oxygen sensor at 900° C., Nd211-20% Nd123 shows a resistance value that is two or more orders of magnitude higher than the resistance value of Nd123. This shows that even when Nd123 is added as a co-material to Nd211, the electrical insulating function is still sufficiently secured.

That is, in the oxygen sensor element, electric current hardly flows through the heat insulating layers made of Nd211-20% Nd123, and thus the heat insulating layers do not lose the electrical insulating function for the sensing layer, so that the sensor output is not affected.

<Oxygen Reactivity Evaluation Results>

Figure 9:
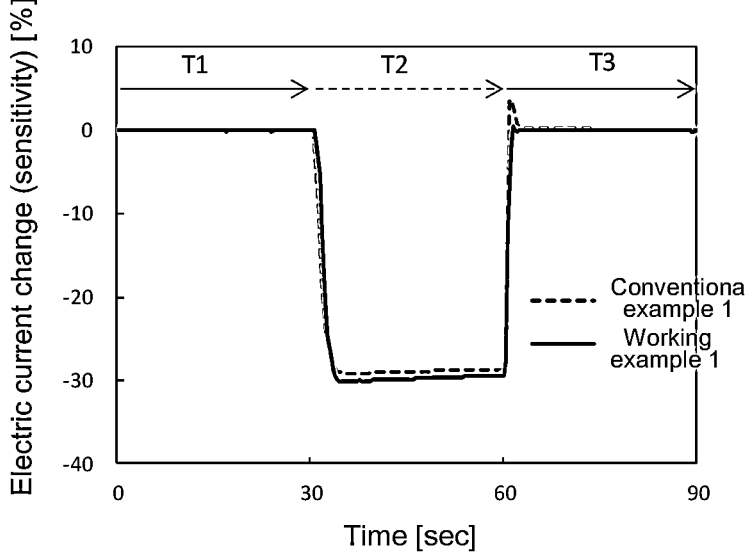
FIG. 9 is a diagram showing oxygen reactivity evaluation results of a test sample having a conventional composition (first conventional example) and a test sample according to the embodiment (first working example), which function as oxygen sensors.

FIG. 9 shows oxygen reactivity evaluation results of a test sample having the conventional composition and a test sample as a first working example according to the embodiment, which function as oxygen sensors. The test sample (first conventional example) having the conventional composition is an element made only of Nd123 without forming a heat insulating layer, and having the same dimensions as those of the first working example.

Here, the test samples are kept in an environment of standard air (21% oxygen concentration) in time period T1 of FIG. 9. In subsequent time period T2, they are kept in an environment having 1% oxygen concentration. In subsequent time period T3, they are kept in the environment of standard air (21% oxygen concentration). In FIG. 9, the horizontal axis represents time [seconds], while the vertical axis represents electric current change (sensitivity) [%].

It is understood from FIG. 9 that the amount of change (responsiveness) in sensor output in both the first working example and the first conventional example is 30%, and thus there is no significant difference in oxygen reactivity between the test sample of the first working example and the test sample of the first conventional example. Moreover, from the fact that the rise and fall of electric current change at respective change-points of oxygen concentration at time periods T1→T2→T3 is steep, it is understood that there is no difference in oxygen reactivity (equal sensor output and equal response speed) between the test sample of the first working example and the test sample of the first conventional example.

When power consumption in each of the test samples of the first working example and the first conventional example is calculated from the current-voltage characteristics, for example, the first working example could reduce the power consumption to 0.40 W, compared to the power consumption of 0.47 W in the first conventional example. Therefore, it can be understood that it is possible for the first working example to improve electric power saving by approximately 20% compared to the first conventional example.

Figure 10:
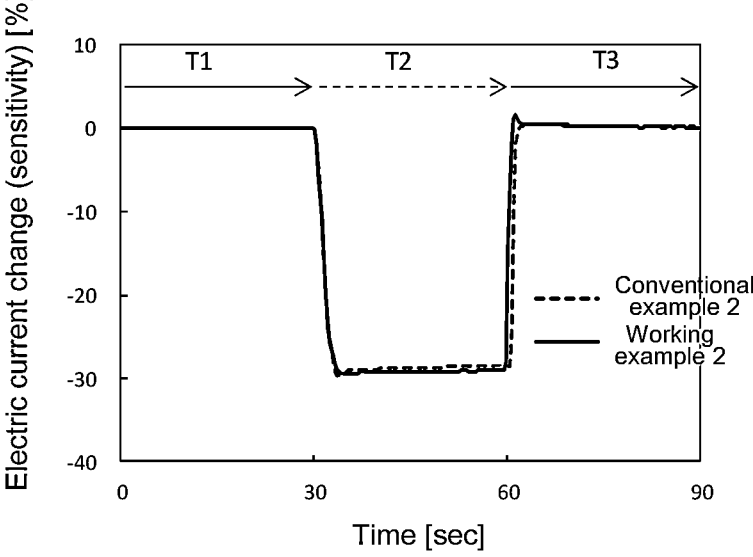
FIG. 10 is a diagram showing oxygen reactivity evaluation results of a test sample having the conventional composition (second conventional example) and a test sample according to the embodiment (second working example), which function as oxygen sensors.

FIG. 10 shows oxygen reactivity evaluation results of a second working example as an oxygen sensor, which has a sensing layer made of the composition Nd123_x-0.4 generated by Nd substitution in Nd123. The test sample (second conventional example) having the conventional composition is an element made only of Nd123x-0.4 without forming a heat insulating layer, and having the same dimensions as those of the first and second working examples. It is understood that the second working example also has oxygen reactivity similar to the oxygen reactivity of the first working example and the second conventional example. When the power consumption in the second working example is calculated in the same manner as the first working example, the power consumption in the second working example is 0.48 W, compared to 0.61 W in the second conventional example. Therefore, it is understood that the second working example can also achieve electric power saving without losing sensor characteristics (sensor output and response speed) of the oxygen sensor.

Taking into account the mechanical strength, mass productivity, etc. of the oxygen sensor element, there is a limit to electric power saving by means of solely reducing the electric current value of current flowing through a thinned element.

Therefore, the oxygen sensor element according to the embodiment has a sandwich structure in which the sensing layer is sandwiched between the heat insulating layers, thereby reducing the amount of heat dissipated from the element to achieve electric power saving. Particularly, since the amount of heat dissipation by radiation is proportional to the fourth power of the element surface temperature according to Stefan Boltzmann's law, reduction in the surface temperature by forming the heat insulating layers is effective. Accordingly, it is possible to downsize a battery used to operate the oxygen sensor using the oxygen sensor element, which improves the portability of the oxygen sensor as a device.

<Oxygen Sensor>

The oxygen sensor using the oxygen sensor element according to the embodiment has heat-generating place (hot spot) in the central portion of the oxygen sensor element, which functions as an oxygen concentration detector. An oxygen sensor 10 shown in FIG. 4 has a structure in which the oxygen sensor element 1 is stored inside the cylindrical glass tube 24 made of heat-resistant glass, which is a protecting member for the oxygen sensor element 1. In order for the oxygen sensor 10 to be electrically connected to the outside, metal conductive caps (mouthpieces) 22a and 22b made of copper (Cu), for example, are embedded in either side of the glass tube 24.

Silver (Ag) wires (the lead wires 6a and 6b in FIG. 1) attached to either end portion of the oxygen sensor element 1 are electrically connected to the respective conductive caps 22a and 22b using a lead-free solder and arranged such that the longitudinal direction of the oxygen sensor element 1 is the same as the axial direction of the glass tube 24, so that the oxygen sensor element 1 does not touch the glass tube 24.

Gas (oxygen) to be measured flows smoothly into the glass tube 24 via air holes 23a and 23b, which are provided on end surface sides of the conductive caps 22a and 22b, respectively, resulting in the oxygen sensor element 1 exposed to that gas, thereby allowing accurate measurement of oxygen concentration in the ambient atmosphere.

The glass tube 24 of the oxygen sensor 10 has a glass tube diameter of 5.2 mm, glass tube length of 20 mm, and air hole diameter of 2.5 mm, for example, thereby making the oxygen sensor element 1 having the dimensions given above (0.35 mm×0.35 mm×5 mm) exchangeable via the air holes 23a and 23b of the glass tube 24.

Note that the protecting member of the oxygen sensor element 1 may be a ceramic case, a resin case, etc. aside from the glass tube described above. Moreover, the connection between the silver (Ag) wires 6a and 6b attached to the oxygen sensor element 1 and the respective conductive caps 22a and 22b may be carried out through a joining method such as lead soldering, welding, caulking, etc.

Furthermore, while omitted from the drawing, in the oxygen sensor, which uses the oxygen sensor element according to the embodiment, electric current flows through the oxygen sensor element according to peripheral oxygen concentration when a predetermined voltage is applied to the oxygen sensor by a power source. Therefore, the oxygen sensor has a configuration for measuring oxygen concentration in the atmosphere to be measured based on the value of electric current measured with an ammeter.

The structure and shape of the oxygen sensor element are not limited to the rod-like shape having the sandwich structure as described for the oxygen sensor element 1 shown in FIG. 1. For example, as an oxygen sensor element 70 shown in FIG. 11, the outer surface of a columnar ceramic sintered body 75 made of Nd123 may be covered in its entirety with a heat insulating layer 74 made of Nd211-20 mol % Nd123. Then, a pair of electrode portions 73a and 73b are formed on either longitudinal end portion of the sensor element, and lead wires 76a and 76b are attached to the respective electrode portions to form the sensor element into a columnar shape in its entirety.

Figure 11:
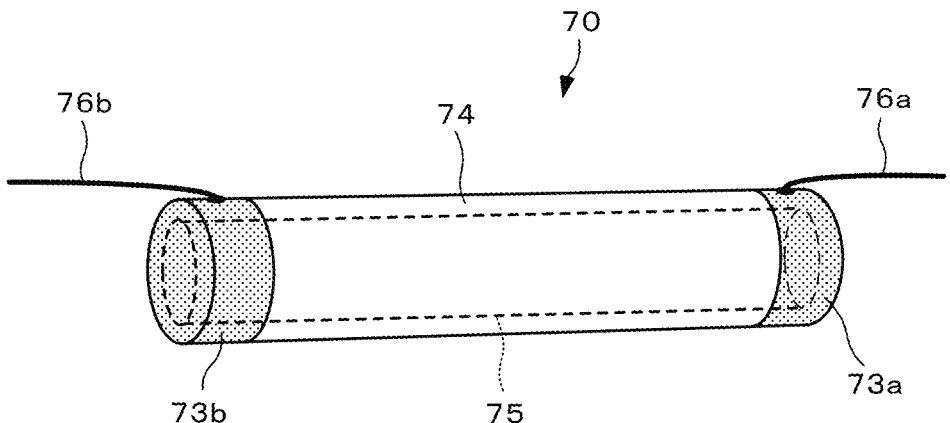
FIG. 11 is an external perspective view of an oxygen sensor element according to a modification.

The oxygen sensor element 70 having the configuration shown in FIG. 11 can also achieve electric power saving by the heat insulating layer 74 which reduces the amount of heat dissipated by radiation from the ceramic sintered body 75. Moreover, since the heat insulating layer 74 is porous, the sensing performance of the oxygen sensor element 70 is prevented from being impaired by the heat insulating layer 74.

As described above, the oxygen sensor element according to the embodiment has a structure in which the outer surface of the ceramic sintered body as a sensing layer made of the composition $LnBa_2Cu_3O_{7-\delta}$ (Ln denotes rare earth element) is covered with heat insulating layers. A heat insulating material having the composition $Ln_2BaCuO_5$ is used for the heat insulating layers, and that composition $Ln_2BaCuO_5$ is added with 20 mol % of $LnBa_2Cu_3O_{7-\delta}$.

As a result, a sintering behavior of the sensor material for the sensing layer and a sintering behavior of the heat insulating material for the heat insulating layers are close to each other. Therefore, separation of the layers on the interface does not occur during baking, and thus the strength is improved, so that the mass productivity of the oxygen sensor element can be ensured. Furthermore, the layered structure in which the sensing layer is sandwiched between the heat insulating layers makes it possible to bake these layers simultaneously. For example, when the oxygen sensor element is incorporated into a protecting member such as a glass tube, the sensor portion is not directly grasped, etc. This makes manufacturing of the oxygen sensor easy and improves the mass productivity of the oxygen sensor.

Still furthermore, the sensor material and the heat insulating material can coexist, and no reaction occurs between them during baking. In addition to that, the layered structure which minimizes the possibility of the sensing layer being exposed to the outside can reduce the amount of radiant heat, allows the oxygen sensor element to have strength against disturbances caused by outside gas, etc., and can maintain the sensor sensitivity of the oxygen sensor element using the hot spot phenomenon. Along with that, it is also possible to achieve electric power saving by improving heat insulating properties.

Improvement in heat cycle capability during use of the sensor can also be expected by adding the composition $LnBa_2Cu_3O_{7-\delta}$ to the heat insulating material for the heat insulating layers.

DESCRIPTION OF REFERENCE NUMERALS 1, 70: Oxygen sensor element
3a, 3b, 73a, 73b: Electrode portion
4a, 4b, 74: Heat insulating layer
5, 15: Sensing layer
6a, 6b, 76a, 76b: Lead wire
10: Oxygen sensor
22a, 22b: Conductive cap
23a, 23b: Air hole
24: Glass tube
75: Ceramic sintered body

The invention claimed is:

1. An oxygen sensor element that is made of a ceramic sintered body for detecting oxygen concentration based on an electric current value or a resistance value measured when a voltage is applied to electrodes provided at either end portion of the ceramic sintered body, wherein
   heat insulating layers represented as a composition formula $Ln_2BaCuO_5$ (Ln denotes rare earth element) are arranged so as to cover a predetermined portion on an outer surface of the ceramic sintered body, excluding the electrodes.

2. The oxygen sensor element according to claim 1, wherein a co-material represented as a composition formula $LnBa_2Cu_3O_{7-\delta}$ (Ln denotes rare earth element, and δ denotes oxygen non-stoichiometry) is added to the heat insulating layers.

3. The oxygen sensor element according to claim 2, wherein an addition quantity "a" [mol %] of the co-material is 0<a≤25.

4. The oxygen sensor element according to claim 1, wherein the Ln is Nd (neodymium).

5. The oxygen sensor element according to claim 1, wherein the oxygen sensor element has a layered structure in which an outer surface of the ceramic sintered body excluding the electrodes is sandwiched between the heat insulating layers bidirectionally, and a part of the ceramic sintered body is exposed.

6. The oxygen sensor element according to claim 5, wherein a thickness t1 [μm] of the ceramic sintered body in a layered direction is 10≤t1≤200, and thicknesses t2 and t3 [μm] of the respective heat insulating layers, between which the ceramic sintered body is sandwiched, in the layered direction are 50≤(t2, t3)≤400.

7. The oxygen sensor element according to claim 1, wherein the oxygen sensor element has a structure in which an outer surface of the ceramic sintered body excluding the electrodes is covered in its entirety with the heat insulating layer.

8. The oxygen sensor element according to claim 1, wherein the ceramic sintered body is formed into a linear shape.

9. An oxygen sensor using an oxygen sensor element which functions as an oxygen concentration detecting element, wherein the oxygen sensor element is made of a ceramic sintered body for detecting oxygen concentration based on an electric current value or a resistance value measured when a voltage is applied to electrodes provided at either end portion of the ceramic sintered body, wherein
   heat insulating layers represented as a composition formula $Ln_2BaCuO_5$ (Ln denotes rare earth element) are arranged so as to cover a predetermined portion on an outer surface of the ceramic sintered body, excluding the electrodes.

10. The oxygen sensor according to claim 9, wherein the oxygen sensor element is stored in a protecting tube having air holes on either end.

11. The oxygen sensor according to claim 9, wherein a co-material represented as a composition formula $LnBa_2Cu_3O_{7-\delta}$ (Ln denotes rare earth element, and & denotes oxygen non-stoichiometry) is added to the heat insulating layers.

12. The oxygen sensor according to claim 11, wherein an addition quantity "a" [mol %] of the co-material is 0<a≤25.

13. The oxygen sensor according to claim 9, wherein the Ln is Nd (neodymium).

14. The oxygen sensor according to claim 9, wherein the oxygen sensor element has a layered structure in which an outer surface of the ceramic sintered body excluding the electrodes is sandwiched between the heat insulating layers bidirectionally, and a part of the ceramic sintered body is exposed.

15. The oxygen sensor according to claim 14, wherein a thickness t1 [μm] of the ceramic sintered body in a layered direction is 10≤t1≤200, and thicknesses t2 and t3 [μm] of the respective heat insulating layers, between which the ceramic sintered body is sandwiched, in the layered direction are 50≤(t2, t3)≤400.

16. The oxygen sensor according to claim 9, wherein the oxygen sensor element has a structure in which an outer surface of the ceramic sintered body excluding the electrodes is covered in its entirety with the heat insulating layer.

17. The oxygen sensor according to claim 9, wherein the ceramic sintered body is formed into a linear shape.

18. A method for manufacturing an oxygen sensor element having a structure in which a predetermined portion on an outer surface of a ceramic sintered body as a sensing layer is covered with heat insulating layers, comprising the steps of:
   molding slurries, which are formed respectively by mixing raw materials for the ceramic sintered body together and by mixing raw materials for the heat insulating layers together, into a sheet form to manufacture a first sheet member and second sheet members;
   cutting each of the first sheet member and second sheet members into a predetermined size;
   layering the cut first sheet member and second sheet members so as to have respective predetermined thicknesses to form a layered body with the layered first sheet member sandwiched between the layered second sheet members in a vertical direction;

cutting the layered body into a predetermined size and a predetermined shape to manufacture a sensor element;

baking the sensor element; and forming a pair of electrodes on either end portion of the baked sensor element, wherein in the baking step, the first sheet member and second sheet members are baked simultaneously.

\* \* \* \* \*